(12) United States Patent
Brunsveld et al.

(10) Patent No.: US 6,262,329 B1
(45) Date of Patent: Jul. 17, 2001

(54) WATER VAPOR PERMEABLE, PRESSURE SENSITIVE ADHESIVE COMPOSITION

(75) Inventors: Gerrit H. Brunsveld, Zutphen; Johannes T. Minnigh, Eefde, both of (NL)

(73) Assignee: National Starch & Chemical Company Investment Holding Corporation, Wilmington, DE (US)

( * ) Notice: Subject to any disclaimer, the term of this patent is extended or adjusted under 35 U.S.C. 154(b) by 0 days.

(21) Appl. No.: 08/369,944

(22) Filed: Jan. 9, 1995

Related U.S. Application Data

(63) Continuation of application No. 07/934,060, filed on Aug. 21, 1992, now abandoned, which is a continuation of application No. 07/662,099, filed on Feb. 28, 1991, now abandoned.

(51) Int. Cl.[7] .............................. A61F 13/00; A61F 15/00
(52) U.S. Cl. .......................... 602/54; 604/307; 523/111; 602/52
(58) Field of Search .................... 602/52, 54, 56; 604/307; 523/111; 424/448; 128/849

(56) References Cited

U.S. PATENT DOCUMENTS

| | | | |
|---|---|---|---|
| 3,645,835 | 2/1972 | Hodgson | 161/146 |
| 3,725,122 | 4/1973 | Reinhard et al. | 117/122 P |
| 3,975,570 | 8/1976 | Ono et al. | 428/355 |
| 4,140,115 | 2/1979 | Schonfeld | 428/411 |
| 4,163,822 | 8/1979 | Walter | 428/304 |
| 4,181,752 | 1/1980 | Martens et al. | 427/54.1 |
| 4,337,325 | 6/1982 | Shah | 525/205 |
| 4,372,303 | 2/1983 | Grossman et al. | 128/132 D |
| 4,374,520 | 2/1983 | Grossman et al. | 128/132 D |
| 4,379,881 | 4/1983 | Peck | 523/111 |
| 4,413,621 | 11/1983 | McCracken et al. | 128/156 |
| 4,510,197 | 4/1985 | Shah | 428/220 |
| 4,657,006 | 4/1987 | Rawlings et al. | 604/307 |
| 5,009,224 | 4/1991 | Cole | 604/307 |
| 5,028,484 | 7/1991 | Martin et al. | 428/352 |
| 5,035,687 | 7/1991 | Sandbank | 604/307 |
| 5,194,550 | 3/1993 | Rance et al. | 526/318.25 |
| 5,804,214 * | 9/1998 | Wong et al. | 424/448 |
| 5,962,013 * | 10/1999 | Wong et al. | 424/448 |

FOREIGN PATENT DOCUMENTS

| | | |
|---|---|---|
| 0 062 682 | 10/1982 | (EP) . |
| 0 147 067 | 7/1985 | (EP) . |
| 0 194 881 | 9/1986 | (EP) . |
| 0 267 554 | 5/1988 | (EP) . |
| 1 381 185 | 1/1975 | (GB) . |
| WO88/01877 | 3/1988 | (WO) . |

* cited by examiner

*Primary Examiner*—Paul B. Prebilic
(74) *Attorney, Agent, or Firm*—Cynthia L. Foulke; Eugene Zagarella, Jr.

(57) ABSTRACT

A water vapor permeable, pressure sensitive adhesive composition comprising a hydrophilic, all acrylic polymer system, free of additives and having enhanced water vapor transmission which contains a significant high amount of hydroxyalkyl acrylate/methacrylate. This adhesive composition is particularly useful in surgical or medical dressing applications.

8 Claims, No Drawings

WATER VAPOR PERMEABLE, PRESSURE SENSITIVE ADHESIVE COMPOSITION

This application is a continuation of application Ser. No. 07/934,060 filed Aug. 21, 1992 and now abandoned which, in turn, is a continuation of application Ser. No. 07/662,099 filed Feb. 28, 1991 and now abandoned.

BACKGROUND OF THE INVENTION

This invention relates to a water vapor permeable, pressure sensitive adhesive composition with enhanced water vapor transmission and which is useful in preventing skin damage by excess water sweat in skin contact applications such as medical and surgical dressing tapes.

During the last several years, there has been much activity in developing pressure sensitive adhesives in water or moisture vapor permeable wound dressings, bandages, and drapes for use in the medical field. It has been found that these moisture vapor permeable, pressure sensitive adhesive dressings provide an improved surgical covering or bandage which speeds the natural wound healing process, while also protecting the wound site. In general, the wound dressings, bandages and surgical drapes allow water vapor to escape from a wound site while preventing liquid water from either entering or escaping from the site. In addition, bacteria is also prevented from passing through the wound dressing, thereby protecting the wound site from bacterial invasion.

Typically, these wound dressings, bandages, and surgical drapes all comprise a membrane layer which incorporates the desired physical characteristics to attain the moisture vapor permeability while preventing liquid water and bacteria from passing through the membrane. In addition, one surface of the membrane incorporates an adhesive which provides the desired pressure sensitive adherence for securing the membrane to the wound site and retaining the membrane in the desired position.

Moisture vapor permeable, pressure sensitive adhesive membranes are typically applied to a patient as a flat sheet, ranging in size from a few square inches to one or two square feet. In order to achieve the desired results, these moisture vapor permeable, pressure sensitive adhesive membranes are extremely thin and pliable. In this way, the desired permeability is provided, and membranes are able to conform to the shape of the patient's body or skin.

Moisture vapor permeable thin films coated with adhesive and which are suitable for application to the skin have been disclosed, for example, in British Patent No. 1,280,631 and in U.S. Pat. No. 3,645,835, as well as European Patent Application Nos. 51935, 81987, 117632 and 178740 and U.S. Pat. Nos. 4,372,303, 4,374,520 and 4,413,621. The known dressings of this type in commercial use have proved useful because the microscopically continuous nature of the adhesive layer and the film prevents ingress of bacteria into the wound.

These dressings have the added advantage that they do not cause maceration of healthy skin to which they may be applied because both the film and the adhesive layer are moisture vapor permeable and generally provide the dressing with a moisture vapor transmission rate (MVTR) of between 300 and 800 g/m$^2$/24 hr. at 37° C. and 100% to 10% relative humidity difference.

However, disadvantages which may arise with known incise drapes include the possibility that if the patient sweats profusely, the adhesive may be affected and the drape may lift away from the skin and thereby compromise the sterility of the operation site.

Similarly with commercially available intravenous access site dressings (I.V. dressings), although the adhesives employed are moisture vapor permeable, the moisture vapor transmission rate (MVTR) of the adhesive when present as a continuous film is not sufficiently high to permit rapid evaporation of moisture through a dressing which has been applied to an exuding site. The result of using such an adhesive can cause the formation of a moist area which can predispose the area to bacterial growth.

Thin film dressings known for use as wound dressings also suffer from the disadvantage that the MVTR of the moisture vapor permeable adhesive when present as a continuous film is not sufficiently high to permit rapid evaporation of moisture from a dressing which has been applied to an exuding wound. The result of using such an adhesive can cause the formation of an unsightly blister which can predispose the area to leakage and lead to bacterial contamination.

One method of overcoming the disadvantages associated with known thin film dressings is to provide the adhesive layer as a macroscopically discontinuous layer in the form of a porous or a pattern spread layer as disclosed in European Patent No. 91800. Such a layer is coated onto a continuous moisture vapor permeable or water absorbent backing layer so that the dressing remains bacteria-proof while also possessing a high moisture vapor transmission rate. However, the discontinuous nature of the adhesive layer can give rise to other disadvantages. The edges of the dressing may lift at the adhesive free areas. The discontinuous adhesive layer may allow exudate, such as in the case of wound or IV dressings, to spread away from the wound or access site over the skin which may cause trauma to the skin. The exudate may ultimately reach the edge of the dressing thereby providing a possible route by which bacteria might reach the wound or site. A discontinuous adhesive layer may allow local drying out of the wound and hence lead to scab formation. None of these occurrences are conducive to wound healing and may lead to a traumatic removal of the dressing.

It would be advantageous therefore if a dressing could be provided with an adhesive present as a continuous layer whereby the above disadvantages of grossly discontinuous adhesive layers can be avoided. It would also be advantageous if the dressing had a greater moisture vapor transmission rate. A dressing of this type is disclosed in WO 88/01877 and involves a thin film adhesive dressing comprising a support layer having a continuous coating on one side of a gel adhesive which is not self adherent and which is a hydrophilic gel containing polyurethane residue.

For many years, the pressure sensitive adhesives that have been used for attachment of these dressing materials to the skin surface were natural rubber based, and therefore they contained the usual chemical additives, such as resins, plasticizers, anti-oxidants, etc. The foregoing listed chemical additives, in addition to others, are potentially irritating to human skin. In addition, as the pressure sensitive adhesive and, in some cases, the dressing materials were occlusive and water vapor non-permeable by nature, the adhesive sheet materials led to water accumulation thereunder. The accumulated water would then over hydrate and soften the outer layers of the skin (stratum corneum) thus causing what is referred to as skin maceration. Additionally, the stratum corneum of the macerated skin is easily further damaged when the pressure sensitive adhesive coated sheet material is removed. Therefore, in order to prevent the widely prevalent moisture caused maceration of skin, the pressure sensitive adhesive coated sheet materials should preferably be composed of water vapor permeable adhesive substrate backings and non-irritating pressure sensitive adhesives.

Many of the modern surgical adhesive dressings and bandages employ an acrylic based pressure sensitive adhesive, which is much more permeable to water than the prior art rubber based occlusive adhesive compositions. Although acrylic based pressure sensitive adhesives are less traumatic to human skin than those which are rubber based, they are not without their inherent disadvantages. Especially in applications where the pressure sensitive adhesive coated dressing sheet material is repeatedly applied to and then removed from the same area of the skin surface, e.g., as in the changing of a medical or surgical dressing, or when in place over a prolonged period of time, a significant local skin damage or water induced maceration can result.

Conventional acrylic-based pressure sensitive adhesive compositions are generally single component materials, comprised of copolymers of alkyl acrylate ($C_1$–$C_{12}$) esters with polar monomers such as acrylic acid, acrylonitrile, acrylamide, etc. Optional modifying monomers which may also be copolymerized with alkyl acrylate esters are methyl or ethyl acrylate, alkyl ($C_1$–$C_8$) methacrylates, styrene, vinyl acetate, etc.

British Patent No. 2,070,631A to R. F. Peck, teaches the copolymerization of n-butyl acrylate, 2-ethylhexyl acrylate and acrylic acid to produce a polyacrylate having a K-value of from 90 to 110 claimed to result in a satisfactory water vapor permeability for use with medical dressings.

E. Schonfeld (U.S. Pat. No. 4,140,115) has proposed the incorporation of a polyol, such as polyoxyalkylene glycol, in the acrylic adhesive mass for use in surgical and/or medical bandages or tapes, which are claimed to result in less skin damage upon their removal.

Ono, et al., (U.S. Pat. No. 3,975,570) has proposed to improve the water vapor permeability of conventional acrylic pressure sensitive adhesives by blending therewith hydroxyethyl cellulose.

K. R. Shah (U.S. Pat. No. 4,337,325) has described blending alkyl acrylic acid copolymers with certain proportions of N-vinyl lactam homopolymers and copolymers to obtain pressure sensitive adhesives having increased water vapor permeabilities.

H. Reinhard, et al. (U.S. Pat. No. 3,725,122), discloses a pressure sensitive adhesive comprising a copolymer of primary and/or secondary alkyl acrylate ($C_4$–$C_{12}$) esters, of which at least 25 percent are derived from alkanols having 6 to 12 carbon atoms, tertiary alkyl ($C_4$–$C_{12}$) esters, N-vinyl pyrrolidone (1 to 10 percent by weight), and olefincally unsaturated monomers (such as acrylic acid, acrylamide, etc.) containing reactive groups.

U.S. Pat. No. 4,181,752 to Martens, et al., discloses a process for the free radical polymerization of acrylic monomers by means of ultraviolet irradiation under controlled conditions in order to prepare pressure sensitive adhesives. N-vinyl pyrrolidone and acrylic acid have been mentioned as monomers copolymerizable with alkyl acrylates by the irradiation process.

A water vapor permeable, pressure sensitive adhesive composition useful for surgical and medical bandage applications is disclosed in U.S. Pat. No. 4,510,197 to K. Shah and comprises copolymers of butyl acrylate, N-vinyl-2-pyrrolidone and acrylic acid.

European Patent Application 194,881 discloses emulsion polyacrylate adhesive polymers which are useful as surgical and medical dressings. The polymer compositions contain a copolymerizable sulfonate surfactant to form a stable, water insensitive emulsion and further comprise acrylic residues of alkyl esters of acrylic or methacrylic acid and optionally may contain small amounts (0.3 to 5%) of hydroxylated alkyl esters of acrylic or methacrylic acid While several acrylic based, water vapor permeable adhesive compositions are disclosed in the above mentioned references, there is no disclosure of an all acrylic, single polymer system free of additives having an especially enhanced water vapor transmission.

OBJECTS OF THE INVENTION

An object of the present invention is to provide an improved pressure sensitive adhesive composition.

A further object of the present invention is to provide an improved pressure sensitive adhesive composition suitable for medical and/or surgical dressing materials, including bandage sheeting materials and adhesive tapes.

Another object of the present invention is to provide an enhanced water vapor permeable, pressure sensitive adhesive composition comprising an all acrylic polymer for coating medical and surgical dressing materials.

Still another object of the present invention is to provide an enhanced water vapor permeable, pressure sensitive adhesive, which will cause minimum maceration or damage to contacted skin areas when applying medical or surgical dressings such as adhesive bandages.

A further object of the present invention is to provide a water vapor permeable, pressure sensitive adhesive which is both convenient to use and economical to manufacture.

In order to accomplish the afore stated objectives, an enhanced water vapor permeable, pressure sensitive adhesive composition, suitable for coating medical and/or surgical sheet dressing materials and the like, has been found and comprises an all acrylic polymer of an alkyl acrylate or methacrylate and a selected high amount of an hydroxyalkyl acrylate or methacrylate and optionally a lower alkyl acrylate or methacrylate and glycidyl acrylate/methacrylate.

The present invention yields a pressure sensitive adhesive composition having an improved water vapor transmission rate which results in a reduction in skin lesions caused by the accumulation of moisture under conventional medical and surgical dressings.

SUMMARY OF THE INVENTION

The present invention relates to a water vapor permeable, pressure sensitive adhesive composition comprising a hydrophilic all acrylic polymer system, free of additives and with enhanced water vapor transmission comprising:

a) from about 50 to 80% by weight of alkyl acrylate or methacrylate wherein the alkyl group contains from about 4 to 12 carbon atoms, b) from about 10 to 40% by weight of hydroxyalkyl acrylate or methacrylate wherein the alkyl group contains from about 2 to 4 carbon atoms, c) from about 0 to 40% by weight of alkyl acrylate or methacrylate wherein the alkyl group contains from about 1 to 3 carbon atoms, and d) from about 0 to 1.0% by weight of glycidyl acrylate or methacrylate.

Another embodiment of the present invention relates to a water vapor permeable, pressure sensitive adhesive film coated onto a surgical or medical dressing sheet or backing material wherein the adhesive film is the all acrylic polymer system as described above and the coated surgical or medical dressing having an enhanced water vapor transmission rate.

DETAILED DESCRIPTION

The water vapor permeable all acrylic polymer adhesive composition as used in this invention generally comprises an alkyl acrylate or methacrylate wherein the alkyl group contains from about 4 to 12 and preferably about 4 to 8 carbon atoms and an hydroxyalkyl acrylate or methacrylate where the alkyl group contains from about 2 to 4 carbon atoms and preferably has 2 carbon atoms. Alkyl acrylates and methacrylates of the above type include n-butyl acrylate and 2-ethylhexyl acrylate and the respective methacrylates while typical hydroxyacrylates or methacrylates include hydroxyethyl acrylate, hydroxypropyl acrylate, hydroxybutyl acrylate and the respective methacrylates. Generally about 50 to 80% by weight of the alkyl acrylate or methacrylate based on the weight of adhesive composition will be used and preferably from about 50 to 70% by weight. The amount of hydroxyalkyl acrylate or methacrylate will generally be a selected high amount of from about 10 to 40% by weight, based on the weight of adhesive composition, preferably from about 15 to 35% and more preferably from about 20 to 35%.

In addition to the alkyl and hydroxyalkyl acrylate or methacrylate components, other acrylic containing monomers may also be included in the adhesive composition. This includes from about 0–40% by weight of an alkyl acrylate or methacrylate wherein the alkyl group contains from about 1 to 3 carbon atoms and from about 0 to 1.0% by weight of glycidyl acrylate or methacrylate. In addition, from about 0 to 10% by weight of acrylic acid, preferably glacial acrylic acid may also be included. When referring to the acrylic component materials as used in this invention, the use of the terms acrylic, acrylate and acrylate or methacrylate is intended to include both the respective acrylic and methacrylic counterparts thereof.

The acrylic adhesive polymer composition of the present invention may be synthesized according to any of the bell known polymerization procedures known to those skilled in the art. One way of preparing this composition involves placing a portion of an admixture of selected alkyl acrylates and hydroxyalkyl acrylate along with desired other acrylic components, solvents and an initiator in a reaction vessel, then purging the reaction vessel with nitrogen and heating and refluxing the reaction mixture for several hours, typically about 8 hours. The remainder of the monomeric solution is then added to the viscous reaction product under constant agitation over a period of typically 4 hours while refluxing the solvent. After addition of the monomeric solution is completed, the reaction mixture is maintained under agitation and solvent reflux for an additional period.

The resulting polymer solution can then be coated onto a backing material or substrate such as a smooth surface release coated silicone paper and air dried for several minutes (e.g., 5–10). Drying can be continued typically at 40° C. for 24–48 hours.

The monomeric constituents of the adhesive composition of the present is invention have been specifically selected in order to obtain cohesive and hydrophilic properties that are necessary to yield a suitable water vapor permeable, all acrylic polymer, pressure sensitive adhesive composition.

The relative viscosity (RV) of the desired polymers should be optimized at from about 2 to 5 and preferably 2.5–3.5 in order to obtain the required cohesive adhesive balance of properties. Generally, very high molecular weights of the polymers should be avoided because they will result in poor tack characteristics, whereas very low molecular weight polymers will yield cohesively weak pressure sensitive adhesives.

In order to achieve desired cohesive and adhesive properties of the polymer, a proper balance of its molecular weight (usually from about 200,000 to 1,200,000 MW or more), its polar character, and a glass transition temperature ($T_g$) ranging from about −25° C. to −70° C., is often necessary.

The pressure sensitive adhesives of the invention are used for adhesive surgical and medical dressings where the adhesive composition may be coated onto any of the well known backing materials which are used in the medical or surgical fields. Thus, the backing may be for example, a conventional non-woven fabric, woven fabric knit, paper or synthetic film backing. Preferred backings include porous polyvinyl chloride film, polyurethane film, integral nets and the like. Suitable backing materials for water or moisture vapor permeable adhesive dressings are disclosed in British Pat. No. 1280631 and in European Application 50935, and backings which permit passage of tissue or wound exudate include non woven fabrics, woven fabrics, knits, nets and apertured films.

The backing material may be of any desired shape to provide adhesive coated sheet materials such as adhesive tapes, strips, wound dressings, surgical drapes or the like. The terms adhesive medical or surgical dressings as used herein are intended to include various wound, medical and surgical type dressings such as bandages, drapes, tapes, first aid dressings, strips, sheets, sutures, etc., which are used in dressing or treating wounds and other similar applications.

The pressure sensitive adhesive composition may be applied to the backing by conventional methods and one common technique is applying the composition to the flexible backing or tape on which it is supported during use by coating it in the form of a solution or dispersion in a suitable vehicle such as an organic solvent or water, and evaporating the vehicle; or by coating it in the form of a hot melt free from the vehicle. In order to be useful, pressure sensitive adhesive compositions must possess good tack, good cohesive strength and the desired high degree of adhesion. All of these properties are generally interdependent, a change in one usually causing a change in the others. It is also noted that the adhesive composition may be applied as a complete or all over spread (continuous or discontinuous) to one surface of the backing material or the adhesive may be applied to body-adhering portions only to form, for example, a window dressing, i.e., one in which the wound-covering area of the backing material is not coated with adhesive.

It may be desirable, depending on the nature of the medical or surgical application, to include some form of dressing or absorbent pad which can be attached to the adhesive coated surface. Additionally, it may be desired to cover or protect the adhesive coated surface until it is ready to be used by applying a release paper or other protective type coating.

The thickness and weight of the adhesive coating used in the medical or surgical dressing of this invention can vary according to the particular application in which it is to be used and the moisture vapor transmission properties required in that application. Typically, the thickness can vary from a few microns up to several millimeters (mm). For example, if the dressing is applied to a wound which is generating a large amount of exudate, the absorptive properties of the adhesive layer may be utilized and a thick layer may be desired. Such a large thickness many vary from about 0.5 to 5 mm and more particularly from about 1 to 4 mm. For use on wounds which are generating small or no amounts of exudate a thin layer of adhesive may be desired. Typically such a thin layer may be from 10 to 100 microns and more particularly from 30 to 50 microns.

The adhesive composition of this invention can be used as a coating or film for medical dressings and bandages, such as adhesive coated first aid dressings and compression bandages. For these uses it is preferred that the backing layer has a moisture vapor transmission rate of at least 3,000 liters vapor/m$^2$/24 hours (liters of water vapor per square meter per 24 hours), more suitably at least 4,000, and preferably at least 5,000 at 80% relative humidity difference.

It is desired that adhesive coated medical dressings, i.e., adhesive coating and backing layer, have a moisture vapor transmission rate of at least 1,000 liters vapor/m$^2$/24 hours, preferably at least 1,200 and more preferably at least 1,500 at 40° C. and 80% relative humidity difference. The pressure sensitive adhesive coating or layer used in the present invention can be a continuous or discontinuous layer, for example, a porous layer. It is preferred, however, that the pressure sensitive adhesive layer is a continuous layer. The continuous polymer coating or film used in the invention does not have openings such as holes, pores or micropores which extend completely through the film. Thus, the continuous polymer coating used in the invention does not have any openings or pores which can provide a passageway for liquid water and bacteria through the film. Such a coating therefore can act as a barrier to liquid water or aqueous fluids and bacteria penetrating from the outside of the wound dressing of present invention at the wound site.

The continuous polymer coating used in the invention film desirably has a moisture vapor transmission rate which is sufficient to permit evaporation of absorbed aqueous body fluid from the pressure sensitive adhesive layer of the invention in use, thereby increasing the absorbent capacity of the adhesive product. The continuous polymer coating used in the invention can suitably have a moisture vapor transmission rate of at least 1,000 liters vapor/m$^2$/24 hour, preferably at least 1,200 and more preferably at least 1,500.

This invention also provides a dressing as hereinbefore described in sterile form. Most aptly the sterile dressing is packaged in a bacteria-proof package such as paper or an aluminum foil pouch.

Normally the dressings are provided for use with silicone release paper (or other convenient material) to protect the adhesive. This protector is removed prior to use of the dressing. The dressings may also be provided with a support layer over the film, if required, which support layer is removed on the application of the dressing. Naturally, neither protector or support layer are essential features of the dressing since neither perform any function when the dressing is in use.

The dressing according to this invention is provided in sterilized form and it is self adhesive and is adhered to a sterile, removable protector layer and packaged in a bacterial proof package such as a paper, plastics or aluminum foil pouch. Sterilization may be achieved in conventional manner, e.g., by use of gamma irradiation, heat or ethylene oxide. Suitable forms of removable protectors and support layers as noted above may be used with the dressing.

The dressings of the present invention will be particularly suitable for use in treating wounds which produce large volumes of exudate and also for use as an intravenous dressing (usually abbreviated to I.V. dressing) for securing a catheter or cannula to reduce the risk of infection at the injection site. The dressings of the present invention are particularly suitable in providing a bacteria proof adhesive dressing, which when placed on healthy skin has a sufficient moisture vapor permeability to prevent its maceration. When used on wounds such as ulcers or donor sites which produce large volumes of exudate, the dressings of the invention aid in reducing the amount of exudate retained under the dressing while also aiding in preventing the wound from drying out if it ceases to produce large amounts of exudate. This aids in the healing of the wound.

The nonwoven fabric employed may have absorbent properties. Suitable nonwoven fabrics include those made from cellulosic fibers such as viscose rayon fibers, or other flexible material. The surface which is poorly wettable or non-wettable may be any such surface but preferred materials have been found to be various types of paper coated with a silicone release material. The surface and the viscosity of the coating solution should be chosen such that a continuous coating of the coating solution may be formed on the surface.

The adhesive materials of the invention may find special application in cases where repeated application of the adhesive material to the skin occurs, e.g., where daily removal of dressings to inspect a wound site is necessary. This is because where such repeated application and removal is necessary it has been found that a higher water vapor permeability is required in the adhesive material, and the adhesive materials of the present invention have an increased water vapor permeability by comparison with similar dressings made up from the same backing and adhesive but having continuous pores.

The present invention is further exemplified below by examples thereof in accordance with the preferred embodiments of the invention. In the following examples and throughout this application, all parts and percentages are by weight unless otherwise indicated, and all temperatures are reported in degrees Celsius, unless otherwise specified.

In order to assure that all physical properties of the various membranes were determined in a manner which would allow comparative analysis, the following standard test procedures were employed for all membrane tests.

Test Methods:

1. Moisture or Water Vapor Transmission Rate (MVTR)

Transmission of water vapor through the membrane or sample material is measured in accordance with the procedure described by Brian W. Walter in U.S. Pat. No. 4,163,822 which is incorporated herein by reference. In this "Payne Cup method", 10 mls. of water are added to the cup and a 6.5 cm diameter sample of the material to be tested is clamped above the opening from the cup. In this case where the test material is an adhesive, it should be coated onto a highly permeable backing, e.g., a nonwoven fabric, for support. The arrangement is then placed in an air circulating oven at a temperature of 40° C. and relative humidity of 20%. The difference between the relative humidity inside the cup and the relative humidity outside the cup causes water to diffuse through the test material and the water loss from the cup is measured by weighing. After placing the arrangement inside the oven, the cup and test material are left to equilibrate for two hours. The weight of the cup is then measured and determined again after 4, 22, and 28 hours.

Water vapor permeability is calculated and expressed as liters water vapor at 40° C. and 80% RH (relative humidity) per square meter per 24 hours.

2. 180° Peel Adhesion

Peel adhesion is measured according to Finat Test Method No. 1 (FTM 1) in which the glass plate is replaced by a stainless steel plate, or is measured via Afera Test Method 4001. The 180° peel adhesion is measured as grams/inch (or grams/25 mm).

3. Measurement of Relative Viscosity (RV)

Relative viscosity (RV) for this group of products is a measure for the molecular weight. The test method is adapted from Monsanto Company Test Method No. 13.03.01.06 A. RV is measured as the ratio of outflow times of i) a 2.22% (solids by solids) solution of the adhesive polymer in ethyl acetate, and ii) pure ethyl acetate, for an Oswald—Fensche No. 100 Viscosimeter at 20° C.

EXAMPLES 1 TO 6

In a 2 liter resin kettle equipped with a stirrer, a thermometer, a condenser, and a nitrogen inlet tube, was placed a 100 gram sample of a monomeric solution consisting of varying proportions of 2-ethylhexyl acrylate (EHA), hydroxyethyl acrylate (HEA), methyl acrylate (MA) and glycidyl methacrylate (GMA), as noted in Table I below, along with 50–200 grams of solvent and an initiator.

After a continuous purge of the reaction vessel with nitrogen was started, the monomeric mixture was then heated and allowed to reflux for 0 to 480 minutes, during which period the viscosity of the reaction mixture increased substantially. The remainder of the monomeric solution was then gradually added to the viscous reaction product under constant agitation over a period of 2–4 hours, while reflux of the solvent was maintained. After addition of the monomeric solutions was completed, the reaction mixture was maintained under agitation and solvent reflux for an additional period of 240–360 minutes.

The polymer solution thus prepared was then coated onto a smooth surface release coated silicone paper and air dried for 5 to 10 minutes. Drying was continued at 40° C. for 24 to 48 hours.

The following tables show the moisture or water vapor transmission rate (MVTR), the relative viscosity (RV), and the coating thickness properties of various polymers according to the present invention.

TABLE I

| EX. | HEA | MA | 2 EHA | GMA | RV | MVTR | Coating Thickness (microns) |
|---|---|---|---|---|---|---|---|
| 1 | 25 | 22 | 53 | 0.15 | 2.8 | 1590 | 35.8 |
| 2 | 25 | 22 | 53 | 0.15 | 2.4 | 2400 | 33.2 |
| 3 | 25 | 22 | 53 | 0 | 2.9 | 1140 | 37.3 |
| 4 | 25 | 22 | 53 | 0.15 | 4.6 | 1170 | 42.6 |
| 5 | 15 | 30 | 55 | 0 | 2.9 | 1210 | 39.8 |
| 6 | 35 | 14 | 51 | 0 | 2.7 | 1260 | 42.3 |

RV is relative viscosity.
MVTR is moisture (water) vapor transmission rate liters/m$^2$ at 40° C., 80% RH difference and 24 hours.

Table II shows an increase in the MVTR of the polymer material after increased time intervals.

TABLE II

| | MVTR | | |
|---|---|---|---|
| EX. | AFTER 4 HOURS | 22 HOURS | 28 HOURS |
| 1 | 1245 | 1590 | 2170 |
| 2 | 1565 | 2400 | 3100 |
| 3 | 1075 | 1140 | 1260 |
| 4 | 1200 | 1170 | 1120 |
| 5 | 1025 | 1210 | 1600 |
| 6 | 1240 | 1260 | 1310 |

For comparison purposes, a control sample of a commercial adhesive product containing 5% by weight of hydroxyethyl acrylate was tested in the same manner as the test materials with the results shown below in Table III.

TABLE III

| Sample | Thickness (Microns) | MVTR after 22 Hours |
|---|---|---|
| Control | 42 | 640 |
| Control + 9% PEG (1) | 27 | 800 |
| Control + 10% PEG (2) | 34 | 710 |
| Control + 10% PVP | 27 | 670 |

PEG = poly ethylene glycol
PVP = poly vinyl pirrolidone
(1) PEG in acetone
(2) PEG in Toluene Comparison of Table II with Table III shows the significant increase in MVTR when using significantly higher amounts of hydroxethyl acrylate (HEA) in the polymer. In all cases the MVTR for the present polymer was considerably higher than the values for either the control adhesive alone, or the control admixed with PEG and PVP.

EXAMPLE 7–12

These examples illustrate the preparation of the coatings having specific amounts in parts by weight of specified monomers in the monomer solution.

TABLE IV

| | EXAMPLES | | | | | |
|---|---|---|---|---|---|---|
| | 7 | 8 | 9 | 10 | 11 | 12 |
| Initial Charge | | | | | | |
| Toluene | 7.5 | 7.5 | 7.5 | 4.5 | — | — |
| Monomer soln. | 75 | 75 | 75 | 76.6 | 76.6 | 76.6 |
| Init. soln. | 12.6 | 12.6 | 12.6 | 12.6 | 12.6 | 12.6 |
| EtOAc (ethyl acetate) | 130.1 | 130.1 | 130.1 | 130.1 | 136.1 | 136.1 |
| Monomer Delay (0–120 min.) | | | | | | |
| Monomer soln. | 225 | 225 | 225 | 229.8 | 229.8 | 229.8 |
| EtOAc | 38.1 | 38.1 | 38.1 | 38.1 | 113.6 | 113.6 |
| Initiator Delay (0–240 min.) | | | | | | |
| Init. Soln. | 46.9 | 46.9 | 46.9 | 46.9 | 46.9 | 46.9 |
| Dilution (after 300 min.) | | | | | | |
| EtOAc | 80 | 80 | 80 | 80 | — | — |
| Compositions Monomer Solutions % | | | | | | |
| HEA | 25 | 15 | 35 | 25 | 20 | 20 |
| 2EHA | 53 | 55 | 51 | 53 | 57 | 57.5 |
| MA | 22 | 30 | 14 | 22 | 18 | 20 |
| GMA Soln. | — | — | — | 2.2 | 2.2 | 2.2 |
| GAA (glacial | — | — | — | — | 5 | 2.5 |

TABLE IV-continued

| | EXAMPLES | | | | | |
|---|---|---|---|---|---|---|
| | 7 | 8 | 9 | 10 | 11 | 12 |
| acrylic acid) | | | | | | |
| Initiator solution | | | | | | |
| VAZO (1) | 2.0 | 2.0 | 2.0 | 2.0 | 2.0 | 2.0 |
| EtOAc | 137.9 | 137.9 | 137.9 | 137.9 | 137.9 | 137.9 |
| GMA Soln. | | | | | | |
| GMA | 10.5 | 10.5 | 10.5 | 10.5 | 10.5 | 10.5 |
| EtOAc | 140 | 140 | 140 | 140 | 140 | 140 |
| RV | 2.9 | 2.9 | 2.7 | 3.1 | 2.8 | 2.7 |
| MVTR | | | | | | |
| 4 hours | 1075 | 1025 | 1240 | 1570 | 1300 | 1450 |
| 22 hours | 1140 | 1210 | 1260 | 1570 | 1200 | 1650 |
| 28 hours | 1260 | 1600 | 1310 | — | 1160 | 1770 |
| 180° Peel (grams/inch) | | | | | | |
| after 20 min. | — | — | — | 1540 | 1400 | 1640 |
| after 24 hours | — | — | — | 2000 | 1900 | 2200 |

(1) VAZO = azo-bis-isobutyronitrile (1) VAZO=azo-bis-isobutyronitrile

It will thus be seen that the objects set forth above, among those made apparent from the preceding description, are efficiently attained and, since certain changes may be made without departing from the scope of the present invention, it is intended that all matter contained in the above description shall be interpreted as illustrative and not in a limiting sense.

What is claimed is:

1. A surgical or medical dressing comprising a backing material coated with a continuous water vapor permeable, pressure sensitive adhesive composition comprising a polymer derived from monomers consisting essentially of:
   a) from about 50 to 80% by weight of alkyl acrylate or methacrylate wherein the alkyl group contains from about 4 to 12 carbon atoms;
   b) from about 20 to 40% by weight of hydroxyalkyl acrylate or methacrylate wherein the alkyl group contains from about 2 to 4 carbon atoms;
   c) from about 0 to 35% by weight of alkyl acrylate or methacrylate wherein the alkyl group contains from about 1 to 3 carbon atoms;
   d) from about 0 to 10% by weight of glycidyl acrylate or methacrylate; and
   e) from about 0 to 10% by weight of acrylic acid, the dressing laving a water vapor transmission rate of at least 1000 liters vapor/$m^2$/24 hours at 40° C. and 80% relative humidity difference.

2. The surgical or medical dressing of claim 1, wherein the alkyl group in said hydroxyalkyl acrylate or methacrylate has 2 carbon atoms.

3. The surgical or medical dressing of claim 2, wherein the alkyl group of the alkyl acrylate or methacrylate of group a) contains 4 to 8 atoms.

4. The surgical or medical dressing of claim 3, wherein the water vapor transmission rate is at least 1200 liters vapor/$m^2$/24 hours at 40° C. and 80% relative humidity difference.

5. The surgical or medical dressing of claim 1, wherein the adhesive composition contains from about 20 to 35% by weight of hydroxyalkyl acrylate or methacrylate.

6. The surgical or medical dressing of claim 5, wherein the alkyl group in said hydroxyalkyl acrylate or methacrylate has 2 carbon atoms.

7. The surgical or medical dressing of claim 6, wherein the alkyl group of the alkyl acrylate or methacrylate of group a) contains 4 to 8 carbon atoms.

8. The surgical or medical dressing of claim 7, wherein the water vapor transmission rate is at least 1200 liters vapor/$m^2$/24 hours at 40° C. and 80% relative humidity difference.

* * * * *